United States Patent
Khoo et al.

(10) Patent No.: US 10,245,296 B2
(45) Date of Patent: Apr. 2, 2019

(54) COMPOSITIONS INCLUDING GINGER FOR THE AMELIORATION OR PREVENTION OF INFLAMMATORY CONDITIONS

(71) Applicant: Hill's Pet Nutrition, Inc., Topeka, KS (US)

(72) Inventors: Christina Khoo, Duxbury, MA (US); Inke Paetau-Robinson, Auburn, KS (US); Nolan Frantz, Andover, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/589,345

(22) Filed: May 8, 2017

(65) Prior Publication Data
US 2017/0239314 A1 Aug. 24, 2017

Related U.S. Application Data

(62) Division of application No. 13/519,823, filed as application No. PCT/US2010/062017 on Dec. 23, 2010, now abandoned.

(60) Provisional application No. 61/290,783, filed on Dec. 29, 2009.

(51) Int. Cl.
| | |
|---|---|
| *A61K 36/9068* | (2006.01) |
| *A23K 50/42* | (2016.01) |
| *A23K 10/30* | (2016.01) |
| *A61K 9/00* | (2006.01) |
| *A61K 31/405* | (2006.01) |

(52) U.S. Cl.
CPC .......... *A61K 36/9068* (2013.01); *A23K 10/30* (2016.05); *A23K 50/42* (2016.05); *A61K 9/0056* (2013.01); *A61K 31/405* (2013.01)

(58) Field of Classification Search
CPC .............. A61K 36/9068; A61K 31/405; A61K 9/0056; A23K 50/42; A23K 10/30
See application file for complete search history.

(56) References Cited

U.S. PATENT DOCUMENTS

| | | |
|---|---|---|
| 3,202,514 A | 8/1965 | Burgess |
| 4,997,671 A | 3/1991 | Spanier |
| 4,997,672 A | 3/1991 | DeSimone et al. |
| 5,004,624 A | 4/1991 | Koschak et al. |
| 5,023,103 A | 6/1991 | Ramaswamy ................ 426/626 |
| 5,114,704 A | 5/1992 | Spanier |
| 5,143,854 A | 9/1992 | Pirrung et al. |

(Continued)

FOREIGN PATENT DOCUMENTS

| | | |
|---|---|---|
| CN | 1972600 | 5/2007 |
| JP | H11-266795 | 10/1999 |

(Continued)

OTHER PUBLICATIONS

Mullan et al., "Early Changes in Serum Type II Collagen Biomarkers Predict Radiographic Progression at One year in Inflammatory Arthritis After Biologic Therapy", Arthritis & Rheumatism, vol. 56, No. 9, Sep. 2007, 2919-2928. (Year: 2007).*

(Continued)

*Primary Examiner* — Jianfeng Song (57) ABSTRACT

The invention encompasses pet food compositions for a companion animal that include ginger and methods for enhancing the quality of life of an animal by administering such pet food compositions in the diet of the animal.

11 Claims, 2 Drawing Sheets

(56) References Cited

U.S. PATENT DOCUMENTS

| | | | |
|---|---|---|---|
| 5,339,771 A | 8/1994 | Axelrod | |
| 5,419,283 A | 5/1995 | Leo | |
| 5,532,010 A | 7/1996 | Spanier et al. | |
| 5,916,565 A | 6/1999 | Rose | A61K 36/185 424/756 |
| 5,953,727 A | 9/1999 | Maslyn et al. | |
| 6,156,355 A | 12/2000 | Shields, Jr. et al. | |
| 6,210,701 B1 | 4/2001 | Darland et al. | |
| 6,309,676 B1 | 10/2001 | Lewandowski | |
| 6,379,727 B1 | 4/2002 | Addy | |
| 7,244,463 B2 | 7/2007 | Wadsworth et al. | 426/635 |
| 2002/0064568 A1* | 5/2002 | Rose | A61K 36/185 424/725 |
| 2002/0086333 A1* | 7/2002 | Gahunia | C07D 493/14 435/7.1 |
| 2003/0013639 A1 | 1/2003 | Yurchak et al. | 514/2 |
| 2003/0194423 A1 | 10/2003 | Torney et al. | |
| 2004/0105925 A1 | 6/2004 | Rubio et al. | 426/508 |
| 2005/0112179 A1 | 5/2005 | Khoo | |
| 2005/0112217 A1 | 5/2005 | Khoo | |
| 2005/0112259 A1 | 5/2005 | Qvyjt | |
| 2005/0147697 A1 | 7/2005 | Rosenbloom | A61K 9/0043 424/729 |
| 2005/0158406 A1 | 7/2005 | McPeak et al. | |
| 2005/0186307 A1 | 8/2005 | Axelrod | |
| 2005/0214392 A1 | 9/2005 | McPeak et al. | |
| 2006/0036419 A1* | 2/2006 | Cook | A01K 5/02 705/300 |
| 2006/0045909 A1 | 3/2006 | Friesen et al. | |
| 2006/0078531 A1* | 4/2006 | Sota | A61K 31/192 424/78.14 |
| 2006/0193950 A1 | 8/2006 | Axelrod et al. | |
| 2006/0193962 A1* | 8/2006 | Kamiya | A61K 31/7008 426/615 |
| 2006/0200320 A1 | 9/2006 | Al-Murrani | G06F 19/3475 702/20 |
| 2007/0042972 A1 | 2/2007 | McKeever et al. | |
| 2007/0082089 A1* | 4/2007 | Krammer | A23K 20/174 426/72 |
| 2007/0087108 A1* | 4/2007 | Wadsworth | A23K 10/30 426/635 |
| 2007/0110880 A1 | 5/2007 | Thomas et al. | |
| 2008/0171319 A1* | 7/2008 | Urdea | C12Q 1/6883 435/6.11 |
| 2011/0159500 A1 | 6/2011 | Khoo et al. | |

FOREIGN PATENT DOCUMENTS

| | | |
|---|---|---|
| JP | 2004-196696 | 7/2004 |
| JP | 2007-512029 | 5/2007 |
| JP | 2007-522822 | 8/2007 |
| JP | 2007-238581 A | 9/2007 |
| JP | 2009-516643 | 4/2009 |
| WO | WO 95/011755 | 5/1995 |
| WO | WO 99/032619 | 7/1999 |
| WO | WO 99/032660 | 7/1999 |
| WO | WO 05/053420 | 6/2005 |
| WO | WO 05/053422 | 6/2005 |
| WO | WO 05/079593 | 9/2005 |
| WO | WO 07/048104 | 4/2007 |
| WO | WO-2007048104 | 4/2007 |
| WO | WO 08/103939 | 8/2008 |
| WO | WO 11/075138 | 6/2011 |
| WO | WO2011082106 | 7/2011 |

OTHER PUBLICATIONS

Kaiyadevanighantau, "Formulation ID No. RS6/1206C", TKDL, Edn 1, pp. 213-214, (Retrieved on Feb. 24, 2015).

Ahmed et al., 2000, "Influence of dietary ginger (Zingiber officinales Rose) on oxidative stress induced by malathion in rats," Food and Chemical Toxicology 38:443-450.

Al-Yahya et al., 1989, "Gastroprotective activity of ginger zingiber officinale rose., in albino rats," Amer. J. Chinese Med. 17(1-2):51-56.

Birn et al., 2005, "Megalin binds and mediates cellular internalization of folate binding protein," The FEBS J. 272:4423-4430.

Fyfe et al., 2004, "The functional cobalamin (vitamin $B_{12}$)-intrinsic factor receptor is a novel complex of cubilin and amnionless," Blood 103:1573-1579.

Gupta et al., 2001, "Reversal of pyrogallol-induced delay in gastric emptying in rats by ginger (Zingiber officinale)," Methods Find. Exp. Clin. Pharmacol. 23(9):501-503.

Hagen Pet Foods, 2007, "Adult Alternative Maintenance Small Breed," Database GNPD Mintel AN: 641688.

Hagen, 2008, "Chicken Flavoured Cat Food," Databse GNPD Mintel AN: 1020389.

Holtmann et al., 1989, "The anti-motion sickness mechanism of ginger," Acta Otolaryngol. (Stockholm) 108:168-174.

International Search Report and Written Opinion in International Application No. PCT/US10/062017, dated Mar. 3, 2011.

Kjeldsen et al., 1998, "Markers of coagulation and fibrinolysis as measures of disease activity in inflammatory bowel disease," Scand. J. Gastroenterol. 33:637-643.

Kozyraki, 2001, "Cubilin, a multifunctional epithelial receptor: an overview," J. Mol. Med. 79:161-167.

Naturvet, 2009, "Calming Aid," Database GNPD Mintel AN: 1065556.

Rasatantrasarah, 1990, "Anupana for Dasamula Kvatha (at/55)," Traditional Knowledge Database TKDL p. 697 Formulation ID: RS22/912F.

Written Opinion in International Application No. PCT/US10/062017, dated Nov. 29, 2011.

Yamahara et al., 1988, "The anti-ulcer effect in rats of ginger constituents," J. Ethnopharmacol. 23:299-304.

Yogaratnakarah, 2004, "Ardrakiyasvarasah," Traditional Knowledge Database TKDL p. 127, Formulation ID: RG8/451A.

Mayo Clinic staff, "Crohn's disease", retrieved on Apr. 4, 2013 from http://www.mayoclinic.com/health/crohns-disease/DS00104.

* cited by examiner

COMPOSITIONS INCLUDING GINGER FOR THE AMELIORATION OR PREVENTION OF INFLAMMATORY CONDITIONS

CROSS REFERENCE TO RELATED APPLICATIONS

This application is divisional application of U.S. application Ser. No. 13/519,823, which is a national stage entry under 35 U.S.C. § 371 of International Patent Application No. PCT/US2010/062017, filed 23 Dec. 2010, which claims priority to U.S. Provisional Patent Application No. 61/290,783 filed on 29 Dec. 2009, all of which applications are incorporated herein by reference.

BACKGROUND OF THE INVENTION

Ginger has long been a culinary ingredient, enjoyed particularly for the flavor it provides. Native to southern Asia, ginger is a 2- to 4-foot perennial that produces grass-like leaves up to a foot long and almost an inch wide. Ginger root, as it is called in the grocery store, consists of the underground stem of the plant, with its bark-like outer covering scraped off. Ginger has long been used as a health supplement for humans.

Ginger's modern use dates back to the early 1880s, when it was noticed that ginger-filled capsules reduced nausea during flu, Ginger was then approved as a treatment for indigestion and motion sickness. Ginger has since become widely accepted as a treatment for human nausea. Even some conventional medical texts suggest ginger for the treatment of the nausea and vomiting of pregnancy, although others are more cautious.

Accordingly, the inventors have developed pet food compositions including ginger, which are useful in treating inflammatory conditions, including gastrointestinal disorders and arthritis, and for improvement of the well-being of companion animals, for example, cats and dogs.

SUMMARY OF THE INVENTION

The invention generally encompasses pet food compositions for a companion animal that include an effective amount of ginger to prevent, to ameliorate the symptoms of or to treat, inflammation or an inflammatory disorders in the companion animal, where the inflammation or inflammatory disorder is an arthritic condition or a gastrointestinal disorder. The arthritic condition may be osteoarthritis, rheumatoid arthritis, psoriatic arthritis, ankylosing spondylitis or a local inflammatory joint condition. Gastrointestinal disorders may include irritable bowel disorders and chronic diarrhea.

The pet food compositions of the invention containing ginger may also meet the nutritional requirements for a companion animal (e.g., an amount of protein, an amount of fat, an amount of carbohydrate, and/or an amount of fiber).

The present inventors have examined the effects of ginger in the diet of an animal. The animal may be a companion animal or livestock. The animal may be a dog. The animal may be a cat. Preferred companion animals of the invention are dogs and cats.

The animal may have a condition, disorder or symptom. The condition or disorder may be inflammatory. The condition may be arthritis. The disorder may be inflammatory bowel disorder. The condition or disorder may be a factor of age in the animal. The disorder may be chronic diarrhea. The symptom may be swelling. The swelling may be at a joint in the animal.

In certain embodiments the invention encompasses pet food compositions for a companion animal that are nutritionally complete food compositions or diets for such an animal. For example, food compositions published in The Association of American Feed Control Officials, Inc. (AAFCO) guidelines for nutritionally complete diets for canines or felines are encompassed by the invention.

In certain embodiments, the invention encompasses pet food compositions for a companion animal including at least about 0.5% by weight ginger. In other embodiments, the ginger may be present at about 1% by weight. In other embodiments, the ginger may be present at 1.5% by weight or may be present at about 2% by weight.

In other embodiments, the invention encompasses methods for improving the quality of life of a companion animal by feeding the animal a pet food composition comprising an amount of protein, an amount of fat, an amount of carbohydrate, an amount of fiber and an effective amount of ginger. In certain embodiments, the composition includes at least about 0.5% by weight ginger. In certain embodiments, the invention encompasses pet food compositions for a companion animal that includes at least about 1% by weight ginger. In other embodiments, the ginger may be present at about 1.5% by weight or may be present at about 2% by weight.

In certain embodiments, the method encompasses feeding an animal in need thereof an amount of a composition including ginger, which is effective to enhance the animal's quality of life, wherein enhanced quality of life is evidenced by reduction in inflammatory arthritic conditions or gastrointestinal inflammatory disorders, or chronic diarrhea.

In other embodiments, the invention encompasses methods for preventing, ameliorating the symptoms of, or treating, an arthritic condition or a gastrointestinal inflammatory disorder or chronic diarrhea in a companion animal in need thereof comprising administering to the animal a pet food composition for a companion animal comprising an amount of protein, an amount of fat, an amount of carbohydrate, an amount of fiber and an effective amount of ginger to prevent, ameliorate the symptoms of, or treat, the arthritic condition or gastrointestinal inflammatory disorder or chronic diarrhea in the companion animal.

In other embodiments, the invention encompasses methods for preventing, ameliorating the symptoms of, or treating, an arthritic condition or a gastrointestinal inflammatory disorder or chronic diarrhea in a companion animal in need thereof, comprising administering to the animal a nutritionally complete diet for a companion animal comprising an amount of protein, an amount of fat, an amount of carbohydrate, an amount of fiber and an effective amount of ginger to prevent, ameliorate the symptoms of, or treat, the arthritic condition or a gastrointestinal inflammatory disorder or chronic diarrhea in the companion animal.

In certain embodiments, the arthritic condition may be osteoarthritis, rheumatoid arthritis, psoriatic arthritis, ankylosing spondylitis or a local inflammatory joint condition.

In another embodiment the gastrointestinal inflammatory disorder may be an inflammatory bowel disorder.

In another embodiment the condition may be chronic diarrhea.

In a preferred embodiment the pet food composition is a nutritionally complete pet food diet for a canine or a feline.

Other and further objects, features, and advantages of the present invention will be readily apparent to those skilled in the art.

DETAILED DESCRIPTION

Figure 1:
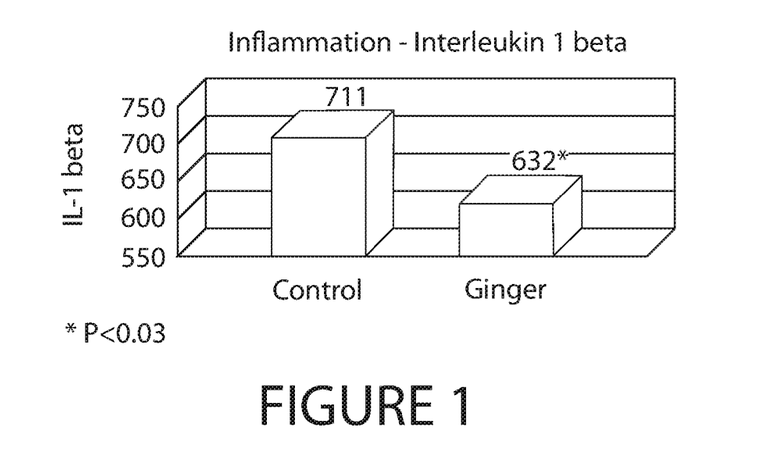
FIG. 1 illustrates the effects on inflammation and interleukin 1-beta (IL-1 beta) of a control pet food composition and an illustrative pet food composition including ginger.
Figure 2:
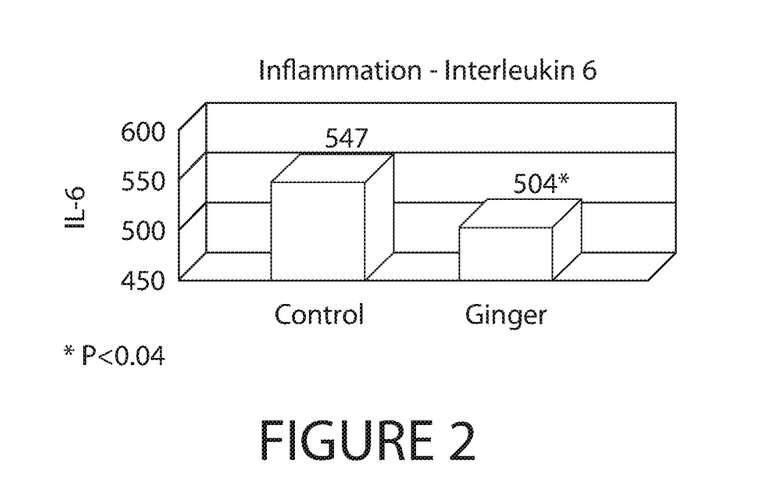
FIG. 2 illustrates the effects on inflammation and interleukin 6 (IL-6) of a control pet food composition and an illustrative pet food composition including ginger.
Figure 3:
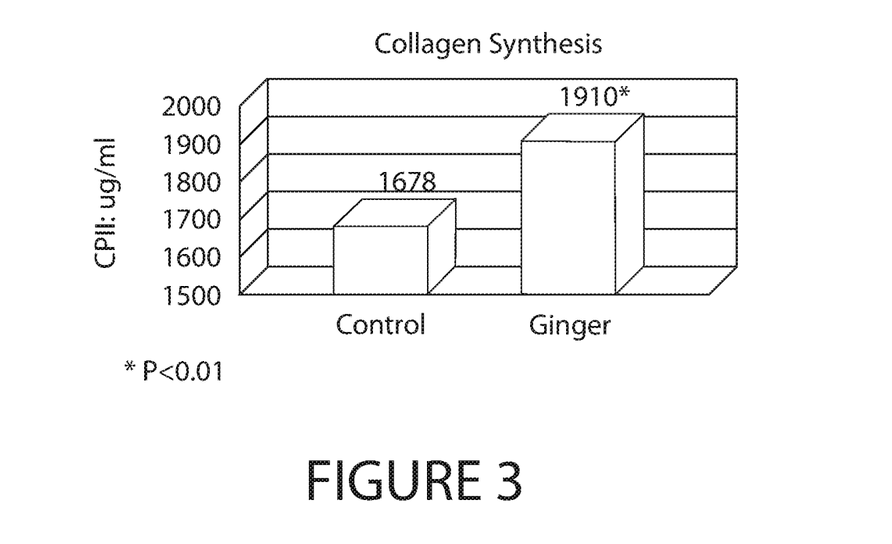
FIG. 3 illustrates the effects on collagen synthesis of a control pet food composition and an illustrative pet food composition including ginger.
Figure 4:
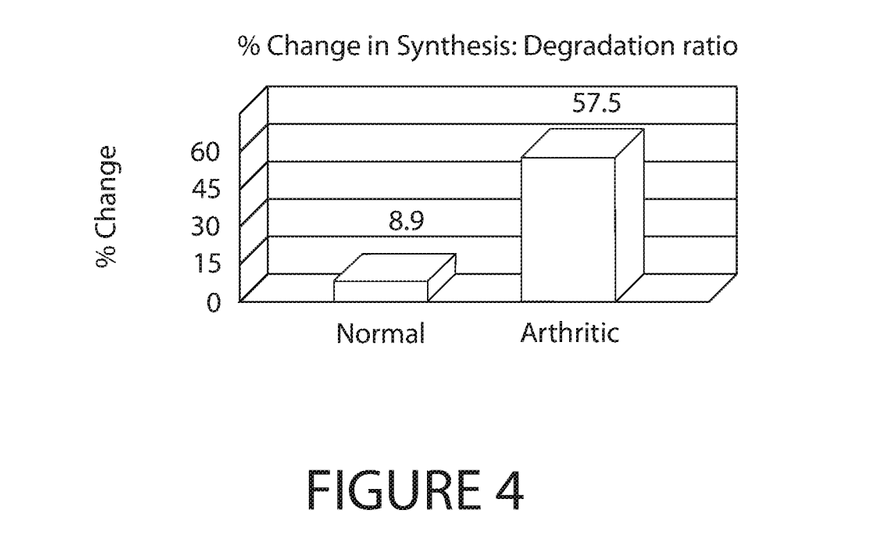
FIG. 4 illustrates the percent change in synthesis: degradation ratio of collagen for a control pet food composition and an illustrative pet food composition including ginger.

It is contemplated that the invention described herein is not limited to the particular methodology, protocols, ingredients and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication, which might be used in connection with the invention.

As used herein and in the appended claims, the singular forms "a", "an", and "the" include plural reference unless the context clearly dictates otherwise.

As used herein, the term "ginger" refers to the plant *Zingiber officinale* and derivatives thereof. By way of example, ginger may include products derived from the leaves, stems, seeds, and roots of a ginger plant. Ginger may be in the form of a ground powder, freshly ground, spray dried, freeze dried, wet root, extract, oil, suspension, oil and water, or solution. The ginger may be cooked or raw. An "extract" of ginger herein is any preparation containing substances extracted from ginger, including fluid extracts, tinctures, essential oils, distillates and oleoresins. Extracts of ginger may be prepared by any of the methods described herein or as known in the art by a skilled worker.

The terms "inflammatory bowel disease" or "IBD" refer to an inflammatory condition of the large and sometimes small intestines. The terms also refer to a group of idiopathic gastrointestinal disorders characterized by continuous or recurring abdominal pain or cramping. The pain may range from mild to severe. Pain is frequently associated with altered bowel motility (e.g., diarrhea, constipation or both).

IBD is also characterized by inflammatory infiltrates within the lamina propria of the gastrointestinal tract. IBD encompasses segmental granulomatous enterocolitis, lymphoplasmacytic enteritis, eoisinophilic gastroenterocolitis, lymphocytic gastroenterocolitis, suppurative enterocolitis and histiocytic colitis. These specific types of IBD are characterized based on the type of inflammatory infiltrate found in the lamina propria. The inflammatory infiltrates can be quite variable in terms of severity and cell types, with lymphocytes and plasma cells being the most common cell types. Inflammatory infiltrates may involve the stomach, small bowel and colon. In the cat, for example, the stomach and small bowel are affected most often. In many cases, multiple segments of the bowel are involved and clinical signs may be mixed, reflecting the broad distribution of mucosal lesions. The severity of IBD varies from mild clinical signs to life-threatening protein-losing enteropathies.

IBD may be marked by any of the following symptoms: abdominal pain, vomiting, diarrhea, hematochezia (bright red blood in stools), weight loss, and various associated complaints or diseases like arthritis, pyoderma gangrenosum, and primary sclerosing cholangitis. IBD may also be a result of the following conditions: Crohn's disease, ulcerative colitis, overactive immune system, collagenous colitis, lymphocytic colitis, ischemic colitis, diversion colitis, Behcet's syndrome, infective colitis, and indeterminate colitis.

Mucosal inflammatory infiltrates are responsible for the clinical manifestations of IBD. Mucosal inflammation disrupts normal absorptive processes. Such disruption results in malabsorption and osmotic diarrhea. Altered gut permeability can result in leakage of fluid, protein and blood into the gut lumen. Malabsorbed fats, carbohydrates, and bile acids result in secretory diarrhea. Inflammatory mediators may also directly trigger intestinal secretion and mucus production by goblet cells. Mucosal inflammatory infiltrates may alter intestinal and colonic motility patterns, a mechanism attributed to the influence of prostaglandins and leukotrienes on smooth muscle. Inflammation of the stomach and small bowel stimulates receptors that trigger vomiting. In cats, for example, the most common clinical signs of IBD are chronic vomiting, diarrhea and weight loss.

The term "chronic diarrhea," or "CD," refers to a chronic or persistent presence of loose or liquid stool. Diarrhea may be caused by a viral, parasitic, or bacterial infection or it may be a symptom of another condition such as dysentery, cholera, botulism, lactose intolerance, appendicitis, celiac disease, fructose malabsorption, pernicious anemia, loss of pancreatic secretions, ulcerative colitis, ischemic bowel disease, bowel cancer, hormone tumors, or Crohn's disease. Diarrhea may be caused by dysfunction in the digestive system. Secretory diarrhea refers to an increase in the active secretion, or an inhibition of absorption. Osmotic diarrhea refers to too much water drawn into the bowels, often by a shift in the concentration of salt ions such as sodium, potassium, and chloride. Motility-related diarrhea is caused by the rapid movement of food through the intestines (hypermotility). Inflammatory diarrhea occurs when there is damage to the mucosal lining or brush border, which leads to a passive loss of protein-rich fluids, and a decreased ability to absorb these lost fluids.

Inflammation refers to a protective attempt by an organism to remove an injurious stimulus and initiate the healing processes for the tissue affected by the injurious stimulus. Inflammation can be classified as either acute or chronic. Acute inflammation is an initial response to harmful stimuli and is achieved by the increased movement of plasma and leukocytes from the blood into the injured tissues. A cascade of biochemical events propagates and matures the inflammatory response, involving the local vasculature, the immune system, and various cells within the injured tissue. Chronic inflammation, or prolonged inflammation, leads to a progressive shift in the type of cells, which are present at the site of inflammation, and is characterized by simultaneous destruction and healing of the tissue from the inflammatory process.

Apoptosis refers to one of the main types of programmed cell death and involves a series of biochemical events leading to a characteristic cell morphology and death, in more specific terms, a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation.

DNA repair refers to a collection of processes by which a cell identifies and corrects damage to the DNA molecules that encode its genome. DNA repair ability of a cell is vital to the integrity of its genome and thus to its normal functioning and that of the organism. Both normal metabolic activities and environmental factors such as UV light and radiation can cause DNA damage, resulting in as many as 1 million individual molecular lesions per cell per day. Many of these lesions cause structural damage to the DNA molecule and can alter or eliminate the cell's ability to transcribe the gene that the affected DNA encodes. Other lesions induce potentially harmful mutations in the cell's genome, which affect the survival of its daughter cells after it undergoes mitosis. Consequently, DNA repair processes are constantly active as it responds to damage in the DNA structure. The rate of DNA repair depends on many factors, such as the particular cell type, age of the cell, and the extracellular environment. A cell that has accumulated a large amount of DNA damage, or one that no longer effectively repairs damage incurred to its DNA, can enter one of three possible states: senescence, apoptosis, or unregulated cell growth.

Oxidative stress refers to an imbalance between the production of reactive oxygen species and a biological system's ability to readily detoxify the reactive intermediates or easily repair the resulting damage. Reactive oxygen species include super oxide, ozone, peroxide and a hydroxyl radical, Oxidative stress causes cellular damage through mechanisms such as damage of DNA, oxidations of polydesaturated fatty acids in lipids, oxidations of amino acids in proteins, and oxidatively inactivate specific enzymes by oxidation of co-factors.

The term "large breed" canine means a canine that generally weighs more than 55 pounds when an adult. The term "regular breed" canine means a canine that weighs less than 55 pounds and more than 20 pounds when an adult. The term "small breed" canine means a canine that weighs less than 20 pounds when an adult. The terms "senior" or "mature adult" refers to the life-stage of an animal. For small or regular breed canines, the "senior" life stage is from about 7 to about 10 years of age. For felines, the "senior" life stage is from about 7 to about 12 years of age. For large breed canines, over 5 years of age represents "senior."

As used herein the term "compositions of the invention" refers to animal dietary food compositions including ginger. The compositions of the invention include ginger in an amount of about 0.5%, about 1%, about 1.5%, about 2%, about 3%, about 4%, about 5%, about 6%, about 7%, about 8%, about 9%, or about 10% by weight. The compositions of the invention may alleviate inflammatory bowel disorder. The compositions of the invention may alleviate diarrhea. The compositions of the invention may alleviate inflammation. The compositions of the invention may relieve arthritic conditions, for example, osteoarthritis, or less common inflammatory joint diseases in companion animals such as rheumatoid arthritis, psoriatic arthritis or other degenerative joint disorders. The compositions of the invention may alleviate cell apoptosis. The compositions of the invention may improve DNA repair. The compositions of the invention may alleviate protein damage. The compositions of the invention may alleviate oxidative stress.

The composition of the invention can be a liquid or a solid food. Where the composition is a liquid, the ginger can be admixed with other components. Where the composition is a solid, the ginger may be coated on the composition, incorporated into the composition or both.

In various embodiments, the ginger may be added to the animal's food. In certain embodiments, the ginger may be added to the animal's food by a compounder or manufacturer at a site or by an animal's caregiver prior to feeding the animal. In other embodiments, the ginger may be added during the processing of an animal's food, such as during and/or after mixing of other components of the composition that is then packaged and made available to consumers. Such processing may include extrusion, canning, baking and the like or any other method of process of producing pet foods that is known in the art.

As used herein, an "ingredient" refers to any component of a composition.

The term "nutrient" refers to a substance that provides nourishment. In some cases an ingredient may comprise more than one "nutrient," for example, a composition may comprise fish oil as an ingredient, the oil itself comprising important nutrients such as eicosapentaenoic acid and docosahexaenoic acid. The distinction in these terms is familiar to one of skill in the art.

As contemplated herein, the compositions of the present invention are meant to encompass nutritionally complete and balanced animal feed compositions that additionally comprise ginger. A "nutritionally complete diet" is a diet that includes sufficient nutrients for maintenance of normal health of a healthy animal on the diet.

Nutritionally complete and balanced pet food compositions are familiar to one of skill in the art. For example substances such as nutrients and ingredients suitable for nutritionally complete and balanced animal feed compositions, and recommended amounts thereof, may be found for example, in the Official Publication of The Association of American Feed Control Officials, Inc. (AAFCO). Atlanta, Ga., 2005, or the National Research Council's *Nutrient Requirements of Dogs and Cats*, The National Academy Press, Washington, D.C., 2006.

For example, a nutritionally complete and balanced dog food composition of the present invention may comprise: about 0 to about 90%, preferably about 5% to 60%, by weight of carbohydrates; about 5% to about 70%, preferably about 10% to about 60%, by weight of protein; about 2% to about 50%, preferably about 5% to about 40%, by weight of fat; about 0.1% to about 20%, preferably about 1% to about 11%, by weight of total dietary fiber; about 0 to about 15%, preferably about 2% to about 8%, by weight of vitamins and minerals, antioxidants, and other nutrients which support the nutritional needs of the animal; and about 0.5% to about 1.5%, preferably 2%, more preferably 1%, by weight of ginger.

For example, a nutritionally complete and balanced cat food composition of the present invention may comprise: about 0 to about 90%, preferably about 5% to 50%, by weight of carbohydrates; about 5% to about 70%, preferably about 20% to about 60%, by weight of protein; about 2% to about 50%, preferably about 5% to about 40%, by weight of fat; about 0.1% to about 20%, preferably about 1% to about 11%, by weight of total dietary fiber; about 0 to about 15%, preferably about 2% to about 8%, by weight of vitamins and minerals, antioxidants, and other nutrients which support the nutritional needs of the animal; and about 0.5% to about 1.5%, preferably 2%, more preferably 1%, by weight of ginger.

As used herein, the term "supplement(s)" include, but are not limited to, a feed used with another feed to improve nutritive balance or performance of the total. Supplements include, but are not limited to, compositions that are fed undiluted as a supplement to other feeds, offered free choice with other parts of an animal's ration that are separately available, or diluted and mixed with an animal's regular feed to produce a complete feed. The Official Publication of The Association of American Feed Control Officials, Inc., for example, contains a discussion relating to supplements. Supplements may be in various forms including, for example, powders, liquids, syrups, pills, encapsulated compositions, and the like.

The term "carbohydrate" as used herein includes polysaccharides (e.g., starches and dextrins) and sugars (e.g., sucrose, lactose, maltose, glucose, and fructose) that are metabolized for energy when hydrolyzed. Examples of carbohydrates suitable for inclusion in the compositions disclosed herein include, but are not limited to, corn, grain sorghum, wheat, barley, and rice.

As used herein, "soluble fiber" refers to dietary fiber that attracts water during digestion and slows the rate of nutrient absorption and is typically found in, e.g., oat bran, seeds, beans, and certain fruits and vegetables such as beet pulp, guar gum, chicory root, psyllium, pectin, blueberry, cranberry, squash, apples, oats, beans, citrus, barley and peas. As used herein, the term encompasses any source of soluble fiber suitable for the compositions disclosed herein as would be evident to one of skill in the art.

The term "antioxidant" means a substance that is capable of reacting with free radicals and neutralizing them. Illustrative examples of such substances include beta-carotene, selenium, coenzyme Q10 (ubiquinone), luetin, tocotrienols, soy isoflavones, S-adenosylmethionine, glutathione, taurine, N-acetylcysteine, vitamin E, vitamin C, lipoic acid and L-carnitine. Examples of foods containing useful levels of one or more antioxidants include but are not limited to, *ginkgo bilboa*, green tea, broccoli, citrus pulp, grape pomace, tomato pomace, carrot spinach, and a wide variety of fruit meals and vegetable meals. It will be understood by one of skill in the art that while units of antioxidants may be provided herein as "ppm", appropriate amounts of antioxidants may also be provided as "IU/kg" where appropriate and customary for a given antioxidant such as, e.g., Vitamin E.

As used herein, "improving" or "enhancing" the quality of life of an animal refers to an improvement or enhancement in one or more characteristics selected from a group consisting of alertness, vitality, protection of cartilage, maintenance of muscle mass, digestibility, and skin and pelage quality. Additionally, improvement/enhancement in blood clotting and platelet activation and aggregation, bone and muscle integrity, inflammatory responses, cartilage degradation and pain response, DNA damage and repair pathways, neural function, glycogen synthesis and degradation, glycolysis, gluconeogenesis, the pentose phosphate pathway and electron transport are also contemplated.

An "improvement" or an "enhancement" in a characteristic or biological pathway refers to a modification in said characteristic or biological pathway such that there is a tendency for the characteristic or pathway to appear and/or function normally and with less tendency to reflect pathological changes in the characteristic or pathway that, e.g., may be typical of a senior animal.

As used herein, methods to "treat" an animal suffering from a disease or disorder is also meant to encompass methods to prevent and/or to ameliorate the disease or disorder as well.

The invention generally encompasses pet food compositions for a companion animal comprising an effective amount of ginger to prevent inflammation or an inflammatory disorder in a companion animal.

In certain embodiments, the effective amount of ginger is at least 0.5% by weight ginger. In other embodiments of the invention ginger is present in a range of about 0.5% to about 2% by weight on a dry matter basis.

In certain embodiments, the companion animal is a dog.
In certain embodiments, the companion animal is a cat.

The compositions in addition to the ginger include at least one component suitable for consumption by a companion animal including, but not limited to, fats, carbohydrates, proteins, fibers, nutritional balancing agents such as vitamins, minerals, and trace elements, and mixtures thereof. One of ordinary skill in the art can select the amount and type of food ingredients for a typical food based upon the dietary requirements of the animal, for example, the animal's species, age, size, weight, health, and function.

The food composition can include up to about 100% of any particular food ingredient or can include a mixture of food ingredients in various proportions. In certain embodiments, the food composition includes a combination of food ingredients in amounts of about 0 wt. % to 50 wt. % fat, 0 wt. % to 75 wt. % carbohydrate, 0 wt. % to 95 wt. % protein, 0 wt. % to 40 wt. % dietary fiber, and 0 wt. % to 15 wt. % of one or more nutritional balancing agents.

In certain embodiments, the fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

In certain embodiments, the protein food ingredient is obtained from a variety of sources such as plants, animals, or both. Animal protein includes meat, meat by-products, dairy, and eggs. Meats include the flesh from poultry, fish, and animals such as cattle, swine, sheep, goats, and the like; meat by-products include lungs, kidneys, brain, livers, stomachs, and intestines. The protein food ingredient may also be free amino acids and/or peptides. Preferably, the protein food ingredient includes meat, a meat by-product, dairy products, or eggs.

In certain embodiments, the fiber food ingredient is obtained from a variety of sources such as vegetable fiber sources, for example, cellulose, beet pulp, peanut hulls, and soy fiber.

In certain embodiments, the nutritional balancing agents are obtained from a variety of sources known to skilled artisans, for example, vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The Association of American Feed Control Officials Inc. (AAFCO) provides recommended amounts of such nutrients for dogs and cats. See, e.g., the Official Publication of The Association of American Feed Control Officials Inc. Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the food compositions may contain additional ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of animal; the animal's age, body weight, general health, sex, and diet; the animal's consumption rate; the type of disease or condition being treated; and the like. Therefore, the component and ingredient amounts may vary widely and may deviate from the preferred proportions described herein.

In certain embodiments, the amount of protein is 5 wt. % to 70 wt. % based on the total weight of the composition.

In certain embodiments, the amount of fat is 2 wt. % to 50 wt. % based on the total weight of the composition.

In certain embodiments, the amount of fiber is 0.1 wt. % to 20 wt. % based on the total weight of the composition.

In certain embodiments, the amount of carbohydrate is 5 wt. % to 90 wt. % based on the total weight of the composition.

In certain embodiments, the pet food composition further comprises any of the following: vitamin E, eicosapentaenoic acid (EPA), docosahexaenoic acid (DHA), other n-3 fatty acids, n-6 fatty acids, crude fiber, soluble fiber, and mixtures of the foregoing ingredients.

In certain embodiments, the ginger is present at about 0.5% by weight.

In certain embodiments, the ginger is present at about 1% by weight.

In certain embodiments, the ginger is present at about 1.5% by weight.

In certain embodiments, the ginger is present at about 2% by weight.

The compositions can contain additional ingredients intended to maintain or improve the health of the animal, for example, supplements, medications, herbs, holistic drugs and compositions, and the like.

The composition of the invention may include one or more additional ingredients to prevent or treat one or more diseases or conditions. The component in the diet which accomplishes this may be an antioxidant or mixture thereof. An antioxidant is a material that quenches a free radical. Examples of such materials include foods such as *Ginkgo Biloba*, citrus pulp, grape pomace, tomato pomace, carrot and spinach, all preferably dried, as well as various other materials such as beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, l-carnitine and the like.

Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The d form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and heat stable form. L-carnitine can be administered in the diet and various derivatives of carnitine such as the salts such as the hydrochloride, fumarate and succinates, as well as acetylated carnitine, and the like can be used.

The quantities administered in the diet, all as wt % (dry matter basis) of the diet, are calculated as the active material, per se, that is measured as free material. The maximum amounts employed should not bring about toxicity. At least about 100 ppm or at least about 150 ppm of Vitamin E can be used. A preferred range of 500 to 1,000 ppm can be employed. Although not necessary, a maximum of about 2000 ppm or about 1500 ppm is generally not exceeded. With respect to Vitamin C, at least about 50 ppm is used, desirably at least about 75 ppm and more desirably at least about 100 ppm. A non-toxic maximum can be employed. The quantity of lipoic acid can vary from at least about 25, desirably at least about 50 ppm, more desirably about 100 ppm. Maximum quantities can vary from 100 ppm to 600 ppm or to an amount which remains non-toxic to the pet. A preferred range is from 100 ppm to 200 ppm. For 1-carnitine about 50 ppm, desirably about 200 ppm, more desirably about 300 ppm for canines are a useful minimum. For felines, slightly higher minimums of l-carnitine can be employed such as about 100 ppm, 200 ppm, and 500 ppm. A non-toxic maximum quantity can be employed, for example, less than about 5,000 ppm. For canines, lower quantities can be employed, for example, less than about 5,000 ppm. For canines, a preferred range is 200 ppm to 400 ppm. For felines, a preferred range is 400 ppm to 600 ppm. Beta-carotene at 1-15 ppm can be employed. Selenium at 0.1 up to 5 ppm can be employed. Lutein at least about 5 ppm can be employed. Tocotrienols at least about 25 ppm can be employed. Coenzyme Q10 at least about 25 ppm can be employed. S-adenosylmethionine at least about 50 ppm can be employed. Taurine at least about 1000 ppm can be employed. Soy isoflavones at least about 25 ppm can be used. N-acetylcysteine at least about 50 ppm can be used. Glutathione at least about 50 ppm can be used. *Gingko Biloba* at least 50 ppm of extract can be used.

In certain embodiments, the compositions further include an effective amount of at least one substance selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In certain embodiments, the composition can be a treat. Treats include compositions that are given to an animal to entice the animal to eat during a non-meal time, for example, dog bones for canines. Treats may be nutritional wherein the composition includes one or more nutrients and/or may have a food-like composition. Non-nutritional treats encompass any other treats that are non-toxic. The composition or components are coated onto the treat, incorporated into the treat, or both. Treats of the invention can be prepared by an extrusion or baking process similar to those used for dry food. Other processes also may be used to either coat the composition on the exterior of existing treat forms or inject the composition into an existing treat form.

In certain embodiments, the composition can be a toy. Toys include chewable toys such as artificial bones. The ginger can form a coating on the surface of the toy or on the surface of a component of the toy, be incorporated partially or fully throughout the toy, or both. There are a wide range of suitable toys currently marketed, for example, U.S. Pat. No. 5,339,771, U.S. Pat. No. 5,419,283, and references disclosed therein. This invention provides both partially consumable toys, for example, toys including plastic components, and fully consumable toys, for example, rawhides and various artificial bones. The invention preferably provides toys for use by a dog or a cat.

In certain embodiments, the companion animal is a senior animal.

In certain embodiments, the inflammatory disorder is arthritis.

In certain embodiments, the inflammatory condition is inflammatory bowel disorder.

In another embodiment, the invention encompasses methods for ameliorating or preventing a gastrointestinal disorder in a companion animal in need thereof comprising administering to the animal a pet food composition for a companion animal comprising an effective amount of ginger to ameliorate or prevent the gastrointestinal disorder in the companion animal.

In certain embodiments, the companion animal is a dog.

In certain embodiments, the companion animal is a cat.

In certain embodiments, the gastrointestinal disorder is inflammatory bowel disorder.

In certain embodiments, the gastrointestinal disorder is diarrhea.

In certain embodiments, the invention encompasses dietary compositions for an animal including at least about 0.5% by weight ginger. In other embodiments, the ginger may be present at about 1% by weight. In other embodiments, the ginger may be present in a range about 0.5% to about 2% by weight on a dry matter basis.

The food composition can include up to about 100% of any particular food ingredient or can include a mixture of food ingredients in various proportions. In certain embodiments, the food composition includes a combination of food ingredients in amounts of about 0 wt. % to 50 wt. % fat, 0 wt. % to 75 wt. % carbohydrate, 0 wt. % to 95 wt. % protein, 0 wt. % to 40 wt. % dietary fiber, and 0 wt. % to 15 wt. % of one or more nutritional balancing agents.

In various embodiments, the companion animals of the invention are the domestic cat (*Felis domesticus*) or the domestic dog (*Canis domesticus*). Other companion animals include, fish, bird and horse.

In various embodiments, the pet food composition can further include corn, poultry meal, palatability enhancer, potassium chloride, iodized salt, calcium carbonate, choline chloride, minerals, mineral premix, preservatives, vitamins, and mixtures thereof. In certain embodiments, the dietary food composition may further include L-tryptophan.

In certain embodiments, the dietary food composition can be administered to a senior animal. In certain embodiments, the dietary composition can be administered to an animal with diarrhea or inflammatory bowel disorder.

In other embodiments, the invention encompasses methods for improving the quality of life of animals by feeding the animal a composition including at least about 0.5% by weight ginger. The compositions include ginger, for example, in amounts of about 1%, 1.5% or 2% by weight of the composition.

In another embodiment, the method encompasses feeding an animal in need thereof an amount of a composition including ginger, which is effective to enhance the animal's quality of life, wherein enhanced quality of life is evidenced by reduction in inflammatory disorders or diarrhea.

In another embodiment, the invention encompasses methods for treating gastrointestinal difficulties in an animal in need thereof including administering to the animal the dietary food composition of the invention. In certain embodiments, the animal may be a companion animal, such as a dog or a cat. In certain embodiments, the gastrointestinal difficulty may be inflammatory bowel disorder or diarrhea.

In another embodiment, the invention encompasses methods for treating inflammation in an animal in need thereof including administering to the animal a dietary food composition of the invention including ginger. In certain embodiments, the inflammation may be inflammatory bowel disorder or arthritis.

The invention encompasses pet food compositions that provide beneficial effects and the methods of preparing and use thereof. The beneficial effects may be anti-inflammatory. The beneficial effects may be anti-arthritic. The beneficial effects may be anti-diarrheal. The present invention provides methods for improving or enhancing the response of an animal to inflammatory bowel disease or diarrhea.

The present invention provides use of ginger to attenuate symptoms associated with gastrointestinal inflammation and diarrhea.

The present inventors have identified the effects of ginger to reduce inflammatory markers and improve markers of cartilage synthesis in cats and dogs with arthritis. Feeding a food containing 0.5% ginger reduced IL-1 beta and IL-6, and tended to lower IFN-gamma markers associated with inflammation/arthritis. In addition, ginger stimulated cartilage synthesis as indicated by a marker (CPII) of collagen synthesis and improved the ratio of collagen synthesis to degradation (CPII:CTXII) with a greater percent increase observed in arthritic cats (57%) compared to non-arthritic (8%). In dogs, feeding a control food+1% ginger resulted in improvements in markers of bone formation, bone turnover, and BAP:NTX ratio. This suggests that dogs fed ginger had improved balance between synthesis and turnover of bone that is normally upset in arthritic animals.

Ginger may be in the form of the ground powder, freshly ground, spray dried or freeze-dried, wet root, extract, or oils, can be incorporated in foods or drinks.

Ginger may be incorporated into a food or used as a nutritional supplement in many different forms including ginger extracts such as ginger powder extracts, ginger fluid extracts, ginger powder, and one or more active compounds of ginger; parts of or whole ginger plants; tinctures thereof; and mixtures thereof. In addition, for any specific active compound of ginger for which suitable synthesis routes are known, the active compound can be prepared synthetically. Preferably, the second ingredient of the nutritional supplement of the present invention is selected from ginger extract, and ginger root powder.

Extracts of ginger can be prepared from fresh or dried ginger root which is prepared by extraction with methanol, ethanol, isopropanol, acetone, ethyl acetate, carbon dioxide, hexane, methylene chloride, chloroform or other solvents or solvent mixtures of comparable polarity.

Ginger contains 1-4% essential oil (oleoresin). Many chemical investigations have been carried out on the constituents of the essential oil of ginger. All together more than 200 different volatile compounds have been identified in the essential oil of ginger. The essential oil of ginger contains a mixture of various terpenes as well as some other non-terpenoid compounds.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-pheillandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, captic acid, caprylic acid, capsaicin, caryophyllene, chavicol, chlorogenic acid, chromium, citral, citronellal, citronellal, cobalt, copper, cumene, curcumin, cystine, delphinidin, Δ-cadinene, elemol, ethyl acetate, ethyl-myristate, farnesal, farnesene, ferulic acid, furfural, γ-aminobutyric acid, γ-terpineine, geranial, geraniol, geranyl-acetate, gingerenone, glutamic acid, glycine, hexahydrocurcumin, histidine, isog-ingerenone-B, isoleucine kaempferol, lecithin, limonene, linoleic acid, magnesium, manganese, methionine, mufa, myrecene, myricetin, myristic acid, neral, neral, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. In addition, mixtures of two or more of these active compounds may be employed.

Without being bound by theory, the benefits of the invention may be the result of physiological effects from the addition of ginger or derivatives thereof to an animal's diet. Similarly, the antioxidants, choline, and other nutrients may play a role in enhancing a senior animal's quality of life.

The invention encompasses food compositions or supplements wherein ginger is present in an effective amount to treat, manage, or ameliorate a condition in an animal. The effective amount of ginger may vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the nutritional supplement or nutritionally complete diet, and the severity of the illness or symptom. It is within the skill of the person of ordinary skill in the art to account for these factors.

A "food" is a nutritionally complete diet for the intended recipient animal (e.g., domestic cat or domestic dog). A "nutritionally complete diet" is a diet that includes sufficient nutrients for maintenance of normal health of a healthy animal on the diet. The methods of this invention utilize compositions that are not intended to be restricted by any specific listing of proteinaceous or fat ingredients or product form. The compositions can be prepared in, for example, a dry, canned, wet, or intermediate moisture form using conventional pet food processes. In some embodiments, the moisture content is from about 5% to about 90% of the total weight of the composition. In other embodiments, the moisture content is from about 65% to about 75% of the total weight of the composition.

The food composition may further contain other ingredients such as corn, poultry meal, grease, palatability enhancers, potassium chloride, iodized salt, calcium carbonate, choline chloride, mineral premix, preservative, vitamin premix. The food may contain protein. The protein may be present in about 5 to 50% by weight. The protein may be animal protein. Animal protein may be part of the total protein. Animal protein may be 50%, 70%, 80%, 90,%, 95%, 99% or 100% of the total protein. The food may contain antioxidants, such as vitamin E. Antioxidant may be present in between about 0.0001 U/g and 3.0 U/g food, such as, e.g., 0.18 U/g. The food may contain eicosapentaenoic acid (EPA) at between 1% and 5% by weight. Fatty acids may also be included such as n-3 and n-6 fatty acids. Fatty acids may be present in about 0.05% to 5% by weight. n-3 fatty acids may be present in about 0.0001% to 2%. n-6 fatty acids may be present in about 0.5% to 5% by weight. The food may contain fiber, such as crude fiber. Fiber may be present in between 0.1% and 20% by weight.

The effective amount of the nutritional supplement will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the nutritional supplement, and the severity of the illness or symptom. It is within the skill of the person of ordinary skill in the to account for these factors.

The ginger dietary foods or supplements of the present invention may be formulated using a safe and effective amount of ginger as discussed herein to provide one or more of the beneficial effects of the invention described herein, and one or more of the optional ingredients which may be obtained from slippery elm or green tea, as well as one or more of the additional optional ingredients described below. The nutritional supplement of the present invention may also be formulated with a pharmaceutically acceptable carrier.

The nutritional supplement of the present invention may be formulated in any orally acceptable dosage form including, but not limited to, capsules, tablets, lozenges, troches, hard candies, powders, sprays, gels, elixirs, syrups, and suspensions or solutions.

An acceptable carrier may include, but is not limited to: (a) carbohydrates including sweeteners, more preferably, fructose, sucrose, sugar, dextrose, starch, lactose, maltose, maltodextrins, corn syrup solids, honey solids, commercial tablet nutritional supplements including Emdex®, Mor-Rex®, Royal-T®, Di-Pac®, Sugar-Tab®, Sweet-Rex, New-Tab®, (b) sugar alcohols including mannitol, sorbitol, xylitol, and (c) various relatively insoluble excipients including dicalcium phosphate, calcium sulfate, calcium carbonate, microcrystalline cellulose and other pharmaceutical tableting ingredients.

Alternatively, the ginger foods or supplements of the present invention may be formulated in liquid form, such as syrups, mouthwashes or sprays with a solvent or dispersant such as water, or other liquids in a pharmaceutically acceptable carrier for repeated delivery of the nutritional supplement to oral and oropharyngeal mucous membranes over a sustained period of time. Preferably, the treatment time is about 5 to 60 minutes, and more preferably about 20 to 30 minutes, so as to permit a prolonged contact of the nutritional supplement with mouth and throat tissues. Alternatively, such formulations can be in a form suitable for dilution with water or other materials prior to use.

The ginger foods or supplements of the present invention may also be formulated in chewable nutritional supplements such as soft candy, gum drops, liquid filled candies, chewing gum bases and dental supplies, such as toothpastes and mouthwashes by further including fructose, sucrose, or saccharin in the nutritional supplement, as needed. In use, the chewable composition is retained in the mouth over a sustained period of time of preferably about 5 to 60 minutes, and more preferably about 20 to 30 minutes.

The ginger foods or supplements of the present invention may be formulated in capsule form with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The ginger foods or supplements of the present invention may be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons and/or other conventional solubilizing or dispersion agents.

Other materials, which may optionally be included in the nutritional supplements of the present invention include inositol, other B-complex vitamins, and anti-inflammatories. Also, ingredients such as sweeteners, flavorants, coloring agents, dyes, preservatives, emulsifying agents, suspending agents, melting agents, excipients, and solvents or diluents such as water, ethanol, propylene glycol, glycerin and various combinations thereof may be included in the ginger foods or supplements of the present invention.

The optional sweeteners, which may be used in the ginger foods or supplements of the present invention include, but are not limited to, saccharin, aspartame, cyclamates, acesulfame K, neohesperidin dihydrochalcone, other sweeteners, and mixtures thereof, which may be added to the carrier in amounts sufficiently low so as not to chemically interact with the main ingredients of the nutritional supplement.

The optional flavorants which may be used in the ginger foods or supplements of the present invention include, but are not limited to, peppermint, peppermint-menthol, eucalyptol wintergreen, licorice, clove, cinnamon, spearmint, cherry, lemon, orange lime, menthol and various combinations thereof.

Although the methods of the invention may improve an animal's quality of life by enhancing all of the above described characteristics or improving all of the described biological pathways, it is not necessary to demonstrate substantial improvements in each of the characteristics or pathways to achieve the "enhanced quality of life" as defined herein.

When the compositions are administered to an animal, the animal experiences an enhanced quality of life, e.g., decreased inflammatory responses, increased collagen synthesis, increased cartilage synthesis, reduced diarrhea, reduced arthritis, decreased cartilage degradation, DNA damage and repair pathways, glycogen synthesis and degradation, glycolysis, gluconeogenesis, the pentose phosphate pathway and the electron transport pathway as indicated by overall beneficial changes at the cellular level. Methods for determining these measurements of quality of life are known to skilled artisans. Potential markers of antioxidant status may include serum vitamin E, ORAC, glutathione peroxidase, alkanels, and/or cell damage indicators. Further, vitality can be measured by various means, including an analysis of metabolism and antioxidant markers, as well as through clinical studies with follow-up questions to participating pet owners. Similarly, cartilage protection can be measured by various means, including an analysis of arthritis biomarkers. Potential arthritis biomarkers may include type II collagen synthesis, matrix metalloproteinase, osteocalcin, alkaline phosphatase activity, COMP, and fragments of cartilage damage. Muscle mass maintenance can be measured by various means, including an analysis of body composition, and digestibility can be measured by various means, including clinical studies with follow-up questions to participating pet owners and animal feeding to determine the percentage of nutrients digested. Skin and pelage quality can be measured by various means, including clinical studies with follow-up questions to participating pet owners.

The methods of the invention are useful for enhancing the quality of life of animals, including primates (e.g., monkeys, chimpanzees, etc.), companion animals (e.g., dogs, cats, horses, etc.), farm animals (e.g., goats, sheep, swine, cattle, etc.), laboratory animals (e.g., mice, rats, etc.), birds (e.g., domestic birds such as canaries, parrots, etc. and commercial birds such as chickens, ducks, turkeys, etc.), rodents (e.g., hamsters, guinea pigs, gerbils, rabbits, hedgehogs, ferrets, chinchillas, etc.), and wild, exotic, and zoo animals (e.g., wolves, bears, deer, etc.). In various embodiments, the animal is a cat, a dog, or a horse.

The food compositions comprise ginger. Ginger may be present at about 0.5%, about 1%, about 1.5%, about 2%, about 3%, about 4%, about 5%, about 6%, about 7%, about 8%, about 9%, or about 10% by weight. The food composition may comprise other ingredients. The other ingredients may be selected from water, protein, fiber, carbohydrate, fat, soluble fiber, insoluble fiber, docosahexaenoic acid (DHA), eicosapentaenoic acid (EPA), omega-3 fatty acids, omega-6 fatty acids, tocopherols, ascorbate, calcium, chloride, cysteine, magnesium, manganese, methionine, phosphorous, potassium, iron, and essential amino acids.

When the composition is an animal food, vitamins and minerals preferably are included in amounts required to avoid deficiency and maintain health. These amounts are readily available in the art. The National Research Council (NRC), for example, provides recommended amounts of such ingredients for farm animals. See, e.g., Nutrient Requirements of Swine (10th Rev. Ed., Nat'l Academy Press, Wash. D.C., 197298), Nutrient Requirements of Poultry (9th Rev. Ed., Nat'l Academy Press, Wash., D.C., 1994), Nutrient Requirements of Horses (Fifth Rev. Ed., Nat'l Academy Press, Wash. D.C., 1989), Nutrient Requirements of Dogs and Cats (Nat'l Academy Press, Wash. D.C., 2006). The Association of American Feed Control Officials Inc. (AAFCO), for example, provides recommended amounts of such ingredients for dogs and cats. See, e.g., the Official Publication of The Association of American Feed Control Officials Inc. Examples of vitamins useful as food additives include vitamin A, B1, B2, B6, B12, C, D, E, K, H (biotin), K, folic acid, inositol, niacin, and pantothenic acid. Examples of minerals and trace elements useful as food additives include calcium, phosphorus, sodium, potassium, magnesium, copper, zinc, chloride, and iron salts.

The methods of the present invention include compositions that may further contain other additives known in the art. Such additives are present in amounts that do not impair the purpose and effect provided by the invention. Examples of additives include, for example, substances with a stabilizing effect, processing aids, substances that enhance palatability, coloring substances, and substances that provide nutritional benefits.

Stabilizing substances include, for example, substances that tend to increase the shelf life of the composition. Potentially suitable examples of such substances include, for example, preservatives, antioxidants, synergists and sequesterants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Additives for coloring, palatability, and nutritional purposes include, for example, colorants (e.g., iron oxide, such as the red, yellow, or brown forms); sodium chloride, potassium citrate, potassium chloride, and other edible salts; vitamins; minerals; and flavoring. Such additives are known in the art. See, e.g., U.S. Pat. No. 3,202,514. See also, U.S. Pat. No. 4,997,671. Flavorants include, for example, dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Flavorants help provide additional palatability, and are known in the art. See, e.g., U.S. Pat. No. 4,997,672. See also, U.S. Pat. No. 5,004,624, U.S. Pat. No. 5,114,704, U.S. Pat. No. 5,532,010, and U.S. Pat. No. 6,379,727. The concentration of such additives in the composition typically may be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

Supplements include, for example, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the Official Publication of The Association of American Feed Control Officials Inc. Supplements may be in various forms including, for example, powders, liquids, syrups, pills, encapsulated compositions, and the like.

Treats include, for example, compositions that are given to an animal to entice the animal to eat during a non-meal time. Treats for canines include, for example, dog bones. Treats may be nutritional, wherein the composition comprises one or more nutrients, and may, for example, have a composition as described above for food. Non-nutritional treats encompass any other treats that are non-toxic.

The invention may further provide ginger in a pet toy, wherein the toy is likely to enter the pet's oral cavity. Toys include, for example, chewable toys. Toys for dogs include, for example, artificial bones. There is a wide range of suitable toys currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). The invention provides both partially consumable toys (e.g., toys comprising plastic components) and fully consumable toys (e.g., rawhides and various artificial bones). It should be further recognized that this invention provides toys for both human and non-human use, particularly for companion, farm, and zoo animal use, and particularly for dog, cat, or bird use.

In preparing a composition for use with the methods of the present invention, any ingredient (e.g., fish oil) generally may, for example, be incorporated into the composition during the processing of the formulation, such as during and/or after mixing of other components of the composition. Distribution of these components into the composition can be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added.

Methods of the present invention include utilizing compositions that can be prepared in a dry form using conventional processes. In one embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

The compositions may also be designed to be easier to chew. Canine and feline foods are typically formulated based on life stage (age), size, body composition, and breed. In the methods of this invention, some embodiments address specific nutritional differences between senior regular or small breed dogs, large breed dogs, and cats.

All percentages expressed herein are on a weight by dry matter basis unless specifically stated otherwise.

This invention is not limited to the particular methodology, protocols, and reagents described herein because they may vary. Further, the terminology used herein is for the purpose of describing particular embodiments only and is not intended to limit the scope of the present invention. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compositions, compounds, methods, and similar information reported therein that might be used with the present invention.

In the specification there have been disclosed typical preferred embodiments of the invention and, although specific terms are employed, they are used in a generic and descriptive sense only and not for purposes of limitation, the scope of the invention being set forth in the following claims. Many modifications and variations of the present invention are possible in light of the above teachings. It is therefore to be understood that within the scope of the appended claims the invention may be practiced otherwise than as specifically described.

SPECIFIC EMBODIMENTS OF THE INVENTION

The invention is further described in the following examples. The examples are merely illustrative and do not in any way limit the scope of the invention as described and claimed.

Example 1

Effect of Ginger in Cats with Chronic Diarrhea and Inflammatory Bowel Disease

The objective of this study was to determine the effect of ginger on the clinical symptoms in cats with chronic diarrhea or inflammatory bowel disease. Two groups of cats, a healthy control group and a test group of cats with chronic diarrhea or inflammatory bowel disease, were fed a baseline food for 2 weeks followed by the same baseline food containing 1% ginger root powder. Stool quality was measured daily.

TABLE 1

Nutrient analysis of control food and food with 1% ginger root powder

| Nutrient analysis | Control | Ginger |
| --- | --- | --- |
| Moisture | 7.9 | 7.63 |
| Protein | 24.74 | 25.02 |
| Carbohydrate | 48.98 | 48.95 |
| Fat | 12.94 | 13.06 |
| Crude Fiber | 1.2 | 1.2 |
| Soluble Fiber | 1.2 | 1.3 |
| Insoluble Fiber | 5.6 | 5.8 |
| DHA | <0.01 | <0.01 |
| EPA | <0.01 | <0.01 |
| Total omega 3 | 0.1 | 0.2 |
| Total omega 6 | 2.49 | 2.53 |
| Total tocopherols IU | 117.8 | 82.3 |
| Ascorbate/stay c (pg/g) | 37 | 20 |
| Calcium | 0.71 | 0.72 |
| Chloride-Soluble | 0.37 | 0.38 |
| Cysteine | 0.29 | 0.29 |
| Magnesium | 0.085 | 0.088 |
| Methionine | 0.63 | 0.67 |
| Phosphorus | 0.7 | 0.72 |
| Potassium | 0.55 | 0.55 |

Table 1 shows the nutrient content of the food. It was found that the food was very similar except for the incorporation of ginger in the food. There were no added fish oil or other antioxidants at levels that may be confounding in the results. Table 2 shows the frequency of stool quality of stools collected daily from the cats during the control food phase and the test food phase.

TABLE 2

The effect of ginger on stool quality in healthy cats and cats with chronic diarrhea

| Clinical Subjects | Diet | Stool quality frequency (# of stools,/% of stools) Stool Grades* | | |
| --- | --- | --- | --- | --- |
| | | 1, 2 | 3 | 4, 5 |
| IBD cats | Control food | 44 (26.2%) | 70 (41.7%) | 54 (32.1%) |
| | Ginger food | 23 (9.8%) | 111 (47.4%) | 100 (42.7%) |
| Normal cats | Control food | 2 (1.5%) | 15 (11.0%) | 11 (87.5%) |
| | Ginger food | 0 (0) | 17 (8.8%) | 176 (91.2%) |

*Stool quality is graded such that 1 and 2 are runny and watery, 3 is semi-formed and gel-like, and 4 and 5 are well formed to hard.)

The results showed that consumption of ginger as incorporated in the kibble significantly improved stool quality in cats with inflammatory bowel disease. It was found that by consuming the kibbles with added ginger cats with inflammatory bowel disease had significantly lower poor stools (9.8 vs. 26.2%) and higher good stools (42.7 vs. 32.1%). The food even slightly improved stool quality in normal cats although the stool quality was already very good. The healthy cats did not have any diarrhea episodes in the 3 week test period and had higher percentage of good stools (91% compared to 88%).

Example 2

Effect of Ginger on Stool Quality in Dogs with Chronic Diarrhea

The objective of this study is to determine the effect of ginger on the clinical symptoms in dogs with chronic diarrhea. Two groups of dogs, a healthy control group and a test group of dogs with chronic diarrhea were fed a baseline food for 2 weeks followed by the same baseline food containing 1% ginger root powder. Stool quality was measured daily.

TABLE 3

Nutrient analysis of control food and food with 1% ginger root powder

| Nutrient analysis | Control | Ginger |
| --- | --- | --- |
| Moisture | 8.9 | 7.5 |
| Protein | 19.5 | 19.8 |
| Carbohydrate | 58 | 58.2 |
| Fat | 8 | 8.2 |
| Crude Fiber | 1.8 | 2.5 |
| Soluble Fiber | 0.6 | 1.6 |
| Insoluble Fiber | 7.9 | 8.6 |
| DHA | 0.01 | 0.01 |
| EPA | 0.01 | 0.01 |
| Total tocopherols IU | 61.2 | 64 |
| Ascorbate/stay c (pg/g) | 67.7 | 81 |
| Calcium | 0.67 | 0.68 |
| Chloride-Soluble | 0.36 | 0.41 |
| Cysteine | 0.25 | 0.26 |
| Magnesium | 0.1 | 0.1 |
| Methionine | 0.43 | 0.44 |
| Phosphorus | 0.6 | 0.6 |
| Potassium | 0.6 | 0.6 |

TABLE 4

The effect of ginger on stool quality in healthy
dogs and dogs with chronic diarrhea

| Clinical Subjects | Diets | Stool quality frequency (# of stools, % of stools) Grades* | | |
|---|---|---|---|---|
| | | 1, 2 | 3 | 4, 5 |
| CD dogs | Control food | 13 (11%) | 9 (8%) | 96 (81%) |
| | Ginger food | 14 (8%) | 9 (5%) | 155 (87%) |
| Normal dogs | Control food | 8 (7%) | 2 (2%) | 109 (92%) |
| | Ginger food | 2 (1%) | 7 (4%) | 187 (95%) |

*Stool quality is graded such that 1 and 2 are runny and watery, 3 is semi-formed and gel like, and 4 and 5 are well formed to hard.

The dietary intervention with 1% ginger resulted in an improvement in clinical symptoms in animals with chronic diarrhea or inflammatory bowel disease.

Example 3

Ginger in Canine and Feline Senior Diet

Methods

Twenty senior cats and twenty senior dogs were utilized to determine the effects of ginger to improve markers of arthritis. In both cats and dogs, 10 had radiographic evidence of arthritis. A control food was fed for 14 days prior to feeding the control food+the test ingredient (Ginger). Ginger was fed for 28 days with samples taken at baseline (day 0) and then at study completion (day 28). Cartilage markers were measured in serum using ELISA kits and procedures to determine biomarker concentrations.

Data were analyzed using a two-way paired t-test to determine the change in marker levels with the hypothesis that the change is different from zero.

Results

Table 5 shows arthritis biomarker values for ten normal and ten arthritic cats fed a control formula enhanced with 1% ginger for 28 days. With the exception of ratios, analysis was performed on natural log transformed values. Means and SED are antilog values of log transformed data. Ratios were calculated and analyzed using untransformed data.

TABLE 5

Biomarker Values for Senior Cats

| Biomarker | Day 0 | Day 28 | SED | P-Value |
|---|---|---|---|---|
| CPII | 1650 | 1894 | 1.03 | 0.0004 |
| IL-1F | 376 | 312 | 1.06 | 0.0061 |
| IL-6F | 178 | 151 | 1.06 | 0.0173 |
| IFN-G | 37.9 | 29.7 | 1.14 | 0.0766 |

Table 6 shows arthritis biomarker values for ten normal and ten arthritic dogs fed canine arthritis control formula enhanced with 1% ginger for 28 days. Means, SED, and ratios were calculated and analyzed using untransformed data.

TABLE 6

Biomarker Values for Senior Dogs

| Biomarker | Day 0 | Day 28 | SED | P-Value |
|---|---|---|---|---|
| BAP | 24.99 | 26.15 | 0.78 | 0.1219 |
| NTX | 14.99 | 12.13 | 0.84 | 0.0458 |
| BAP:NTX Ratio | 1.81 | 2.21 | 0.10 | 0.0249 |

What is claimed is:

1. A method for treating inflammation or an inflammatory disorder in a companion animal in need thereof, comprising:
    measuring a baseline level of expression of one or more inflammatory biomarkers in the companion animal in need thereof;
    treating the companion animal in need thereof by administering to the companion animal a pet food composition comprising an effective amount of ginger to treat the inflammation or inflammatory disorder in the companion animal, wherein the inflammatory disorder is arthritis; and
    measuring a change in the level of expression of the one or more inflammatory biomarkers relative to the baseline level of expression in the companion animal in need thereof, thereby indicating treatment of the inflammation or the inflammatory disorder,
    wherein the companion animal is a cat, and wherein measuring the change in the level of expression of the one or more biomarkers relative to the baseline level of expression consists of measuring an increase in biomarker C-propeptide of type II collagen (CPII).

2. The method of claim 1, wherein the composition further comprises at least one of an amount of protein, an amount of fat, an amount of carbohydrate, and an amount of fiber.

3. The method of claim 2, wherein the amount of protein is about 5 wt. % to about 70 wt. % based on the total weight of the composition.

4. The method of claim 2, wherein the amount of fat is about 2 wt. % to about 50 wt. % based on the total weight of the composition.

5. The method of claim 2, wherein the amount of fiber is about 0.1 wt. % to about 20 wt. % based on the total weight of the composition.

6. The method of claim 2, wherein the amount of carbohydrate is about 5 wt. % to about 90 wt. % based on the total weight of the composition.

7. The method of claim 1, wherein the pet food composition further comprises at least one of corn, poultry meal, palatability enhancer, potassium chloride, iodized salt, calcium carbonate, choline chloride, mineral premix, preservatives, vitamins, and mixtures thereof.

8. The method of claim 1, wherein the pet food composition further comprises L-tryptophan.

9. The method of claim 1, wherein the pet food composition further comprises any of the following: vitamin E, eicosapentaenoic acid (EPA), docosahexaenoic acid (DHA), other n-3 fatty acids, n-6 fatty acids, crude fiber and mixtures thereof.

10. The method of claim 1, wherein the companion animal is a senior animal.

11. A method for treating chronic inflammation in a companion animal, comprising:
    measuring a baseline level of expression of one or more inflammatory biomarkers in the companion animal in need thereof;
    treating the companion animal in need thereof by administering to the companion animal in need thereof a pet food composition comprising fiber, protein, fats, carbohydrates, and an effective amount of ginger to reduce or eliminate the inflammatory response within the companion animal, the amount of the ginger being from 1.5% to 10% by weight of the composition, wherein the chronic inflammation is arthritis; and
    measuring a change in the level of expression of the one or more inflammatory biomarkers relative to the baseline level of expression in the companion animal in need thereof, thereby indicating treatment of the chronic inflammation, wherein the companion animal is a cat, and wherein measuring the change in the level of expression of the one or more biomarkers relative to the baseline level of expression consists of measuring an increase in biomarker CPII.

* * * * *